(12) United States Patent
Beecher

(10) Patent No.: US 8,969,251 B2
(45) Date of Patent: Mar. 3, 2015

(54) GENERATION AND USE OF ISOTOPIC PATTERNS IN MASS SPECTRAL PHENOTYPIC COMPARISON OF ORGANISMS

(75) Inventor: Christopher William Ward Beecher, Ann Arbor, MI (US)

(73) Assignee: Methabolic Analyses, Inc., Chapel Hill, NC (US)

( * ) Notice: Subject to any disclaimer, the term of this patent is extended or adjusted under 35 U.S.C. 154(b) by 1341 days.

(21) Appl. No.: 12/244,555

(22) Filed: Oct. 2, 2008

(65) Prior Publication Data

US 2009/0124518 A1 May 14, 2009

Related U.S. Application Data

(60) Provisional application No. 60/976,923, filed on Oct. 2, 2007.

(51) Int. Cl.
| | | |
|---|---|---|
| *B01D 59/44* | (2006.01) | |
| *C40B 20/08* | (2006.01) | |
| *H01J 49/00* | (2006.01) | |
| *G01N 33/58* | (2006.01) | |
| *G01N 33/50* | (2006.01) | |
| *G01N 33/68* | (2006.01) | |

(52) U.S. Cl.
CPC ............ *H01J 49/0009* (2013.01); *G01N 33/58* (2013.01); *C40B 20/08* (2013.01); *G01N 33/5038* (2013.01); *G01N 33/5082* (2013.01); *G01N 33/6848* (2013.01); *B01D 59/44* (2013.01); *B01J 2219/00527* (2013.01); *B01J 2219/00581* (2013.01); *B01J 2219/00659* (2013.01); *B01J 2219/0072* (2013.01)
USPC .............................................. 506/6; 250/282

(58) Field of Classification Search
None
See application file for complete search history.

(56) References Cited

U.S. PATENT DOCUMENTS

| | | | | |
|---|---|---|---|---|
| 6,391,649 | B1 * | 5/2002 | Chait et al. ..................... | 436/173 |
| 6,790,673 | B1 | 9/2004 | Kingston | |
| 6,849,396 | B2 | 2/2005 | Schneider | |
| 6,940,065 | B2 | 9/2005 | Graber et al. | |
| 6,962,818 | B2 | 11/2005 | Schneider et al. | |
| 7,045,296 | B2 | 5/2006 | Parker et al. | |
| 7,820,963 | B2 * | 10/2010 | Beecher ........................ | 250/282 |
| 7,820,964 | B2 | 10/2010 | Beecher | |
| 2004/0033625 | A1 * | 2/2004 | Aebersold ..................... | 436/518 |
| 2004/0121445 | A1 * | 6/2004 | Marino et al. ............. | 435/252.3 |
| 2004/0195500 | A1 | 10/2004 | Sachs et al. | |
| 2006/0284068 | A1 * | 12/2006 | Amirav et al. ................ | 250/282 |
| 2007/0158542 | A1 | 7/2007 | Bauer et al. | |
| 2007/0176088 | A1 | 8/2007 | Li | |

FOREIGN PATENT DOCUMENTS

| | | |
|---|---|---|
| WO | WO 2009/021056 | 2/2009 |
| WO | WO 2009/021059 | 2/2009 |
| WO | WO 2009/046204 | 4/2009 |

OTHER PUBLICATIONS

Lefers and Holmgren Lab, Minimal Medium, http://groups.molbiosci.northwestern.edu/holmgren/Glossary/Definitions/Def-M/minimal_medium.html, 2004.*
Everly et al (2004) "Quantitative Cancer Proteomics: Stable Isotope Labeling with Amino Acids in Cell Culture (SILAC) as a Tool for Prostate Cancer Research" Molecular & Cellular Proteomics 3(7):729-735, including supplementary data.*
Ong et al (2003) "Properties of 13C-Substituted Arginine in Stable Isotope Labeling by Amino Acids in Cell Culture (SILAC)" Journal of Proteomics Research 2(2):173-181.*
WO 2009/021056 International Search Report.
WO 2009/046204 International Search Report.
WO 2009/021059 International Search Report.
Hellerstein, *Metabolic Engineering* 6:85-100 (2004).
Williams et al., *Experimantal Cell Research* 69:106-112 (1971).
Wu et al., *Anal Biochem* 336:164-171 (2005).
Katajamaa et al., BMC *Bioinformatics* 2005, 6:179; doi:10.1186/1471-2105-6-179.
Rögnvaldsson et al., 2004 *J. Chrom. B*, 807:209-215; doi:10.1016/j.jchromb.2004.04.010.
Johannsen, 1911 *American Naturalist* 45:129-159.
Rögnvaldsson et al., 2004 *J. Chrom. B*, 807:209-215; doi:10.1016/j.jchromb.2004.04.010
Dr. Christopher W. W. Beecher Declaration.
Supporting Slides 1-39.
Manuscript, DeJong and Beecher, "Yeast and the Assessment of the IROA Technology as an accurate Method for the Quantitation of Metabolite Profiles".
Manuscript, DeJong and Beecher, "Addressing the Current Bottlenecks of Metabolomics: IROA, an Isotopic Labeling Technique for Accurate Biochemical Profiling".

* cited by examiner

*Primary Examiner* — Tracy Vivlemore
*Assistant Examiner* — Karen S Weiler
(74) *Attorney, Agent, or Firm* — Husch Blackwell, LLP

(57) ABSTRACT

A method for assaying phenotypic similarity or dissimilarity between organisms is disclosed in which a composite sample of admixed first and second samples is provided. The first, standard sample contains average concentrations of compounds of molecular mass less than about 1000 AMU present in the organism species. The second, assay sample contains compounds of having a similar molecular mass present in the organism whose phenotype is to be assayed. The constituents of both samples are (i) in a liquid medium and (ii) each compound of a sample has the same, first and second respective amounts of first and second stable isotopes of a first atom. The composite sample is mass spectroscopically analyzed for analytes, with the ratio of first to second isotope being determined for each analyte, along with a composite sample median ratio. The ratios for each analyte are compared to the median, with outlying ratios indicating dissimilarity.

16 Claims, 3 Drawing Sheets

GENERATION AND USE OF ISOTOPIC PATTERNS IN MASS SPECTRAL PHENOTYPIC COMPARISON OF ORGANISMS

CROSS-REFERENCE TO RELATED APPLICATION

This application claims benefit of Provisional Patent application No. 60/976,923 entitled "Method for the generation and use of isotopic patterns in mass spectral data" filed on Oct. 2, 2007, U.S. patent application Ser. No. 12/186,381 entitled "Method For Generation And Use Of Isotopic Patterns In Mass Spectral Data Of Simple Organisms" filed on Aug. 5, 2008, now U.S. Pat. No. 7,820,963, and U.S. patent application Ser. No. 12/186,395 entitled "Method For Generation And Use Of Stable Isotopic Patterns In Mass Spectral Data" filed on Aug. 5, 2008, now U.S. Pat. No. 7,820,964 B2, whose disclosures are hereby incorporated by reference.

TECHNICAL FIELD

The present application relates to the creation and use of isotopic patterns in mass spectral analyses for identifying phenotypic similarity or dissimilarity of an assayed organism. More specifically, isotopic patterns are used in a system containing a biological organism to be phenotypically assayed to carry out a phenotypic comparison of complex biological organisms. A contemplated method utilizes predefined and unique isotopic patterns present in compounds known to be in a first phenotype as standards for comparison with compounds present in an assayed, second phenotype.

BACKGROUND ART

The use of stable isotopes for the determination of biological information has a long and illustrious history [see, Hellerstein, *Metabolic Engineering* 6:85-100 (2004)]. The oldest and most frequent such usage is in studies probing metabolism wherein a stable isotope is incorporated into a specific molecule at a specific location. This isotopically-labeled molecule, or "precursor", is fed to an in vivo organism, in vitro cell system, or in vitro cell-free system for either a brief or extended period of time, after which the fate of the isotope is determined, either by use of NMR, mass spectrometry (MS), chemical degradation, or other detection technique.

In contrast to the use of radioactive isotopes, the use of stable isotopes is generally regarded as safe and free of regulation. Although in general, a study typically uses a single isotope incorporated into a specific location in order to achieve a precision in understanding the metabolic fate of a molecule, another embodiment of the use of stable isotopes utilizes wholly-labeled molecules (>99% of an atom is replaced with an isotopic equivalent), or universally-labeled (the isotope is universally distributed within the target molecule at less than saturation levels). There are many known studies in which more than one isotope is incorporated into a target molecule, and all of the isotopic fragments are examined for their differential fates. In all cases, these methods are targeted analyses; i.e., they seek the incorporation of a specific labeled atom into other specific molecules.

Yet another use of stable isotopically labeled compounds is as internal standards for their non-labeled counterparts. In such an experiment an isotopically enriched molecule is added to a sample or extract at a known concentration prior to an analysis, and the final measurement determines the exact concentration of the non-labeled material by comparison. In this type of study, it is not uncommon for a researcher to add more than one isotopically-distinct standard if more than one molecule is to be quantified. Indeed, there are extreme forms where one prepares an extremely complex mixture by growing a complex organism on an isotopically-defined feedstock such that the entire organism is heavily, if not entirely, composed of molecules consisting of only one isotope [Wu et al., *Anal Biochem* 336:164-171 (2005)]. In this situation, the same standard is introduced into all samples, but there is no information carried by the standard other than for purposes of relative quantitation; i.e., the standard has no relation to the experiment at hand. Historically, such standards are carefully constructed to differ from any other analyte by a specific mass difference.

BRIEF SUMMARY OF THE INVENTION

The present invention contemplates a method for assaying phenotypic similarity or dissimilarity (phenotypic comparison) of an assayed, second organism compared to a standard or control, first organism that is often of the same species. A contemplated method comprises the steps of providing a composite sample comprised of an admixture of substantially equal amounts of first and second samples. The first sample is a standard (control) sample that is comprised of average concentrations of a majority of constituent compounds having a molecular mass of less than about 1000 Da (AMU) that are present in a representative sample of the first (control) organism. Those constituent compounds (i) are dissolved or dispersed in a liquid medium, preferably an aqueous medium, and (ii) each constituent compound is comprised of the same, first predetermined amounts of first and second stable isotopes of a first atom.

The second representative sample is an assay sample that is comprised of constituent compounds having a molecular mass of less than about 1000 AMU that are present in a representative sample of the second, test, organism whose phenotype is to be assayed. The constituent compounds (i) are dissolved or dispersed in a liquid medium, preferably an aqueous medium, and (ii) each constituent compound is comprised of the same, second predetermined amounts of first and second stable isotopes of the first atom. The first and the second predetermined amounts of first and second isotopes are different from each other, and the first and second isotopes are other than H or D.

The composite sample prepared for analysis is mass spectroscopically analyzed for analyte peaks. The ratio of first isotope to second isotope is determined for each analyzed analyte peak. The composite sample median isotopic ratio is determined. The ratio of first isotope to second isotope for each analyzed analyte peak is compared with the composite sample median isotopic ratio. An assayed organism whose analyzed peak isotopic ratios significantly deviate from the analyzed peak isotopic ratios of the composite sample median are phenotypically dissimilar from the standard organism. An assayed organism whose analyzed peak isotopic ratios do not significantly deviate from the analyzed peak isotopic ratios of the composite sample median is phenotypically similar to the standard organism.

In another embodiment, a library of phenotypic isotopic peak ratios or profiles of various organisms is prepared and used for comparison to organisms whose identity is unknown or desired to be known. Thus, for example, a library of phenotypic peak ratios for various strains of *E. coli, S. aureus, S.* cerevisiae or the like can be prepared as a catalogue against which unknown organisms can be compared.

BRIEF DESCRIPTION OF THE DRAWINGS

In the drawings forming a portion of this disclosure.

Figure 1:
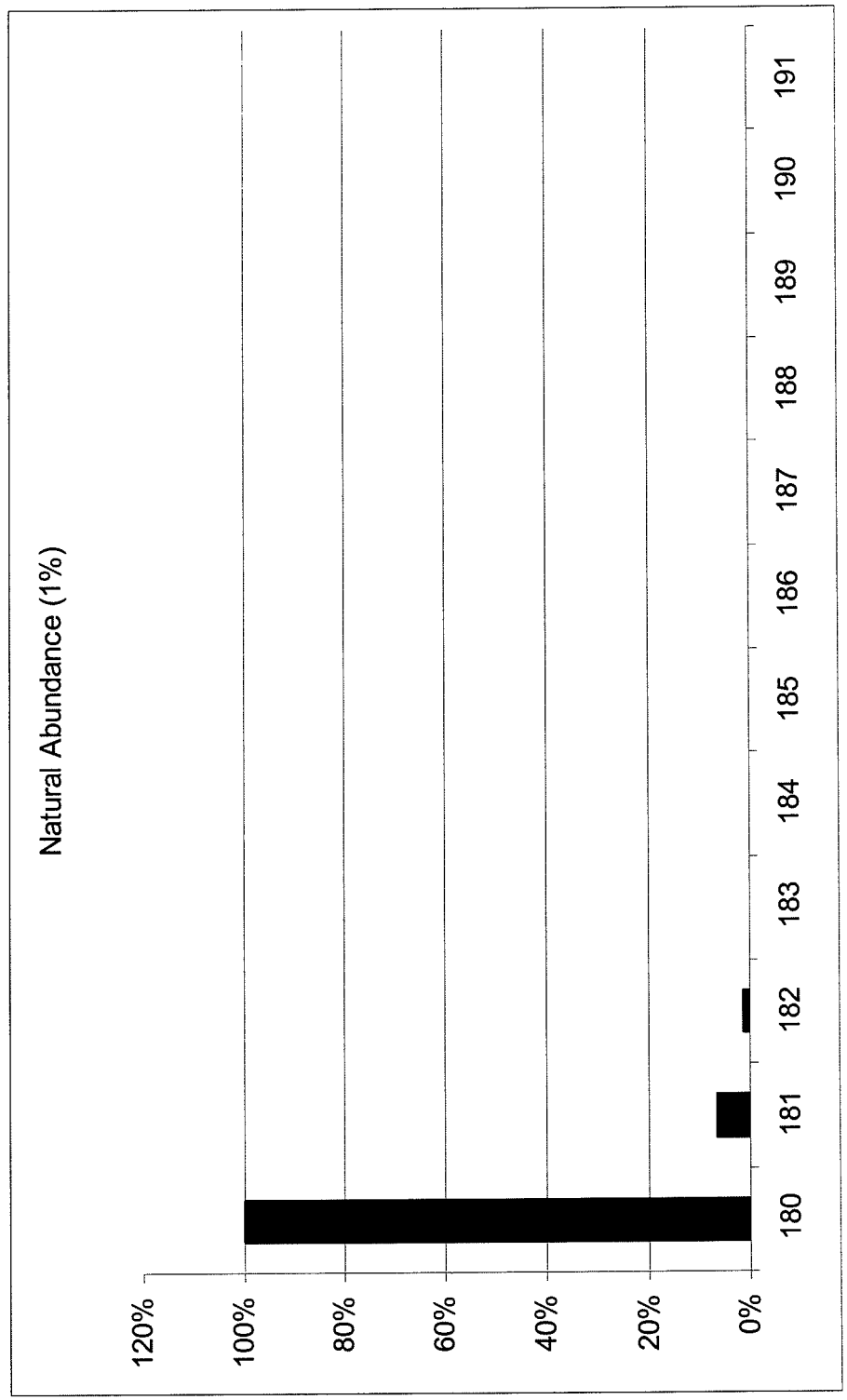
FIG. 1 illustrates a hypothetical mass spectrum obtained by mixing natural abundance C-12 (98.9% C12) glucose with an equivalent amount of C-13 (98.9% C-13) glucose.

The present invention has several benefits and advantages.

One benefit is that by the use of specifically designed isotopic ratios one can identify the source of analyte peaks seen in the spectrum, irrespective of spectral complexity. Specifically, a spectral signal can a) originate from the control culture, or b) experimental culture, or c) be an artifact acquired during sample preparation, or d) originate from the externally applied drug or response inducer, or standard. Each of these classes of compounds has unique characteristics.

One advantage of the invention is that variation that is experimentally introduced; i.e., "noise", is statistically nullified and/or greatly minimized.

Another benefit of the invention is that at the liquid chromatography-mass-spectral interface, there is a loss of signal due to "ion suppression". Ion suppression occurs whenever there is more compound than charge availability. In this situation, some compounds become charged at the expense of other compounds. The variability of ionization efficiency is such that some molecules cannot be accurately quantified. The present method almost fully removes the problem of ion suppression because a compound's ability to ionize is a function of its structure and is not significantly altered by its isotopic distribution.

Still further benefits and advantages of the invention will be apparent to the skilled worker from the disclosure that follows.

DETAILED DESCRIPTION OF THE INVENTION

A phenotype is any observable characteristic of an organism, such as its morphology, development, biochemical or physiological properties, or behavior. Phenotypes result from the expression of an organism's genes as well as the influence of environmental factors and possible interactions between the two. The genotype of an organism is the inherited instructions it carries within its genetic code. Not all organisms with the same genotype look or act the same way, because appearance and behavior are modified by environmental and developmental conditions. Also in the same way, not all organisms that look alike necessarily have the same genotype. This genotype-phenotype distinction was proposed by Wilhelm Johannsen in 1911 to make clear the difference between an organism's heredity and what that heredity produces. [Johannsen, 1911 *American Naturalist* 45:129-159.]

The present invention contemplates a method for identifying phenotypic similarity or dissimilarity (phenotypic comparison) of an assayed, second (test) organism compared to a standard, first organism of the same species. A contemplated method comprises the steps of providing a composite sample comprised of an admixture of substantially equal amounts of first and second samples. The first sample is a standard sample that is comprised of average concentrations of a majority of constituent compounds having a molecular mass of less than about 1000 AMU that are present in a representative population of the standard organism species whose phenotype is to be assayed. Those constituent compounds (i) are dissolved or dispersed in a first liquid, preferably an aqueous, medium, and (ii) each constituent compound is comprised of the same, first predetermined amounts of first and second stable isotopes of a first atom.

The second sample is an assay sample that is comprised of constituent compounds having a molecular mass of less than about 1000 AMU that are present in the second, test, organism whose phenotype is to be assayed. The constituent compounds (i) are dissolved or dispersed in a second liquid, preferably an aqueous, medium, and (ii) each constituent compound is comprised of the same, second predetermined amounts of first and second stable isotopes of the first atom. The first and second predetermined amounts of first and second isotopes are different from each other, and the first and second isotopes are other than H or D.

The constituent compounds of each of the first and second samples are dissolved or dispersed in a liquid medium that is preferably an aqueous composition. The first and second liquid media need not be the same for each sample, but if different, the liquids are preferably miscible. Water alone or a buffered composition can be used as can various combinations of water and alcohols such as ethanol, methanol, 1- or 2-propanol and the butanols. A mixture of 40 percent by volume ethanol in water is a preferred medium. Other liquids that are useful include acetonitrile, pyridine, dimethyl sulfoxide, dimethyl formamide, hexamethyl phosphoramide and the ionic liquids as are discussed in U.S. Pat. No. 6,824,599 and the citations therein.

The composite sample is mass spectroscopically analyzed for analyte peaks. The ratio of first isotope to second isotope is determined for each analyzed analyte peak. The composite sample median isotopic ratio or first profile is determined. The ratio of first isotope to second isotope for each analyzed analyte peak (second profile) is compared with the composite sample median isotopic ratio. An assayed second organism whose analyzed ion peak isotopic ratios significantly deviate from the analyzed ion peak isotopic ratios of the composite sample median are phenotypically dissimilar from the standard organism. An assayed organism whose analyzed ion peak isotopic ratios do not significantly deviate from the analyzed ion peak isotopic ratios of the composite sample median is phenotypically similar to the standard organism. Significant deviation from the sample median is deemed herein to mean two or more standard deviations from the average ratio.

A composite sample is itself comprised of two samples, each of which contains constituent compounds having a molecular mass of less than about 1000 AMU that are present in the first or second organism. The higher molecular weight constituent compounds can be removed before the two samples are admixed to form the composite or after that admixture and prior to the mass spectral analysis. It is presently preferred that the samples be admixed prior to removal of the higher molecular weight components so that the fewest possible manipulations are required to be carried out.

The components of the composite sample are themselves typically separated prior to introduction into the mass spectrometer. That separation can be carried out using gas chromatography, high pressure liquid chromatography (HPLC), size exclusion chromatography, electrophoresis and the like. Various separation techniques can also be combined. Illustrative equipment for use in such separations and analyses include the Agilent 6520 Accurate-Mass Q-TOF LC/MS; Agilent 5975 Series MSD; Thermo-Fisher LTQ; Thermo-Fisher ORBITRAP®; Waters MICROMASS® GCT Premier™; and the Waters LCT Premier™. Separation systems can be part of the mass spectrometer (as in GC) or separate. Further equipment includes the machines known as Waters ACQUITY HPLC®; Agilent Rapid Resolution; and Thermo Surveyor Plus systems.

In order to combine the samples, the samples are uniformly and universally labeled with appropriate isotopes. An element in which there are two stable isotopes that are not significantly distinguished by enzymes or living systems can be used. Carbon (specifically, $^{12}C$ and $^{13}C$) is used for purposes of illustration herein because of its universal applicability; however, additional examples include the isotopes of nitrogen ($^{14}N$ and $^{15}N$), oxygen ($^{16}O$, $^{17}O$, or $^{18}O$), sulfur ($^{32}S$, $^{33}S$, $^{34}S$, or $^{36}S$) chlorine ($^{35}Cl$ and $^{37}Cl$), magnesium ($^{24}Mg$, $^{25}Mg$ and $^{26}Mg$), silicon ($^{27}Si$, $^{28}Si$ and $^{29}Si$), calcium ($^{40}Ca$, $^{42}Ca$, $^{43}Ca$, and $^{44}Ca$), and bromine ($^{79}Br$ and $^{81}Br$).

The use of isotopes that exhibit minimal biological isotope effect is of import. For instance, the use of the isotopes of hydrogen (D or T, which is radioactive and thus not favored) would not be suitable because they frequently cause an observable effect on metabolism due to the fact that the deuterium isotope has a mass that is twice that of hydrogen, and thus, is known to cause a reduction in the kinetics of some enzyme mechanisms but not in others. The discussion that follows considers carbon as an illustrative element for incorporation and use in an assay. However, there are examples where other elemental combinations can provide less broad but specific insights.

Compounds of biological origin are unique in that they are all interrelated through the biological process. A contemplated method extends this truth by creating two populations of almost identical biological potential but requiring that each be based on differing isotopic source material. Thus, each biological sample has a full biochemical complement that is made up of differing isotopic distributions. In the simplest case, two classes of samples are created, e.g. experimental and control. One of these classes, for the sake of this discussion the "standard" or "control", is derived from medium in which the isotopic distribution was primarily carbon thirteen and the other (the "experimental" or "assay sample") is based on medium that was primarily carbon twelve.

Illustratively, where single celled organisms are to be compared, the standard or control, first organism is grown in a first nutrient medium containing predetermined amounts of first and second stable isotopes of a first atom within a nutrient, whereas the experimental second or assayed sample organisms are grown in a second nutrient medium substantially identical to the first nutrient medium but containing different predetermined amounts, compared to said first nutrient medium, of the first and second stable isotopes of that first atom within the nutrient.

Thus, for a system using stable isotopes of carbon [carbon-12 ($^{12}C$) and carbon-13 ($^{13}C$)], the isotopic ratios in this example specifically include a dilution of five to ten percent of one carbon isotope in the other; i.e., one sample is grown on a carbon source (nutrient in a medium) that can be 95% carbon-12 ($^{12}C$) and 5% carbon-13 ($^{13}C$), hereinafter called "C-12 medium", and in such a situation the other sample is grown in mirrored medium that contains a nutrient that contains 95% carbon-13 and 5% carbon-12 in a medium, hereinafter called "C-13 medium". In each of these cases the biological system takes up the nutrient in the medium and grows upon it in such a way as to transform itself so that all of its parts are distinctively identifiable as to their origin.

As used herein, predetermined first and second stable isotope amounts are preferably present in "inverted ratios" of each other such as those discussed immediately above in which the number of the numerator of the first ratio is the number of the denominator of the second ratio, and the number of the denominator of the first ratio is the number of the numerator of the second ratio. Taking the above ratios of 95% and 5%, a first ratio would be 95/5 $^{12}C/^{13}C$ in the C-12 medium, whereas the second, inverted ratio, would be 5/95 $^{12}C/^{13}C$ in the C-13 medium. It is to be understood that a contemplated set of preferred ratios need not be 95/5 and 5/95 and that those numbers are just used for convenience. When these two samples are mixed, intermingled or otherwise composited, the composite sample contains molecules from both the "standard" or "control" (that are made up of a substantial majority; i.e., 90% to 95%, of $^{13}C$) and the "experimental" or "assay sample" (that are made up of a substantial majority; i.e., 90% to 95%, of $^{12}C$). Using the mass distribution for all of compounds identified from such a composite sample one can determine the relative contributions for each compound from either original sample. Deviating significantly from the 90% to 95% ratio taught by this method reduces the potential for interpretation. Consider three cases for isotopic ratios; 1) the natural abundance of $^{12}C$ is approximately 98.9%, whereas the natural abundance of $^{13}C$ is approximately 1.1%, 2) nearly pure (i.e. approaching 100%) of each, or 3) controlled isotopic ratio mixtures. In case 1, natural abundance, every compound will be a collection or mixture of isotopomers that vary in mass due the presence of $^{13}C$ impurity in the $^{12}C$ background (see FIG. 1). Thus, the distribution of these isotopomers as seen in the mass spectrometer will include a number of peaks derived from ions (also called "daughters") that are shifted up to higher mass from the peak (also called "parent") of the majority ion.

Unfortunately, in a majority of biochemicals or metabolites these secondary peaks are quite small and often lost as they are indistinguishable from noise. If one were to create a similar "anti-natural abundance" for $^{13}C$; i.e., 98.9% $^{13}C$ and 1.1% $^{12}C$, then the sample would have the majority peak as the highest mass and show a number of peaks that are shifted down from it at lower masses, but again in the majority of cases these additional peaks are indistinguishable from noise, if they are detectable at all.

Figure 2:
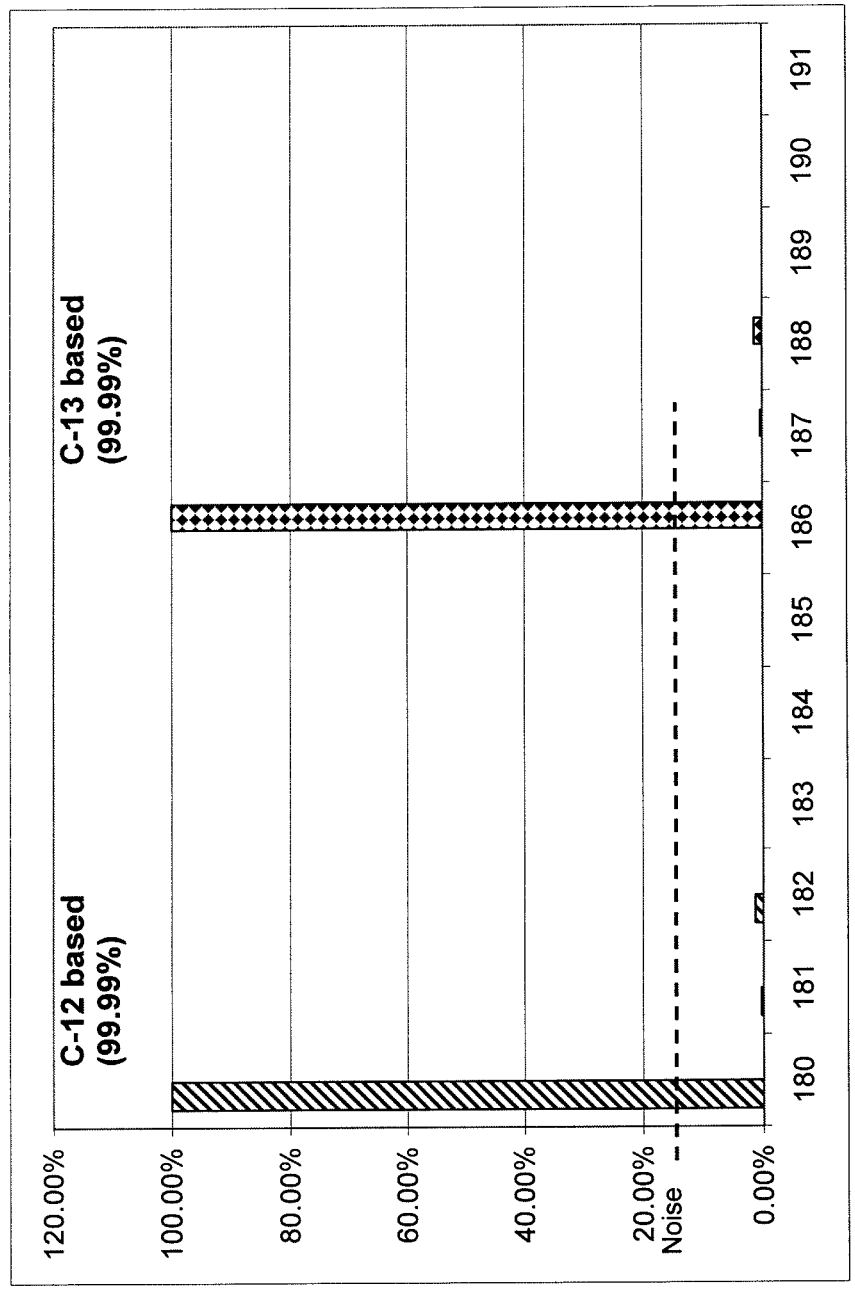
FIG. 2 illustrates a hypothetical mass spectrum obtained by mixing substantially pure natural C-12 glucose on the left (diagonal lines) with an equivalent amount of substantially pure C-13 glucose on the right (diamonds). This situation has been considered optimal in other teachings such as WO 05059566.
Figure 3:
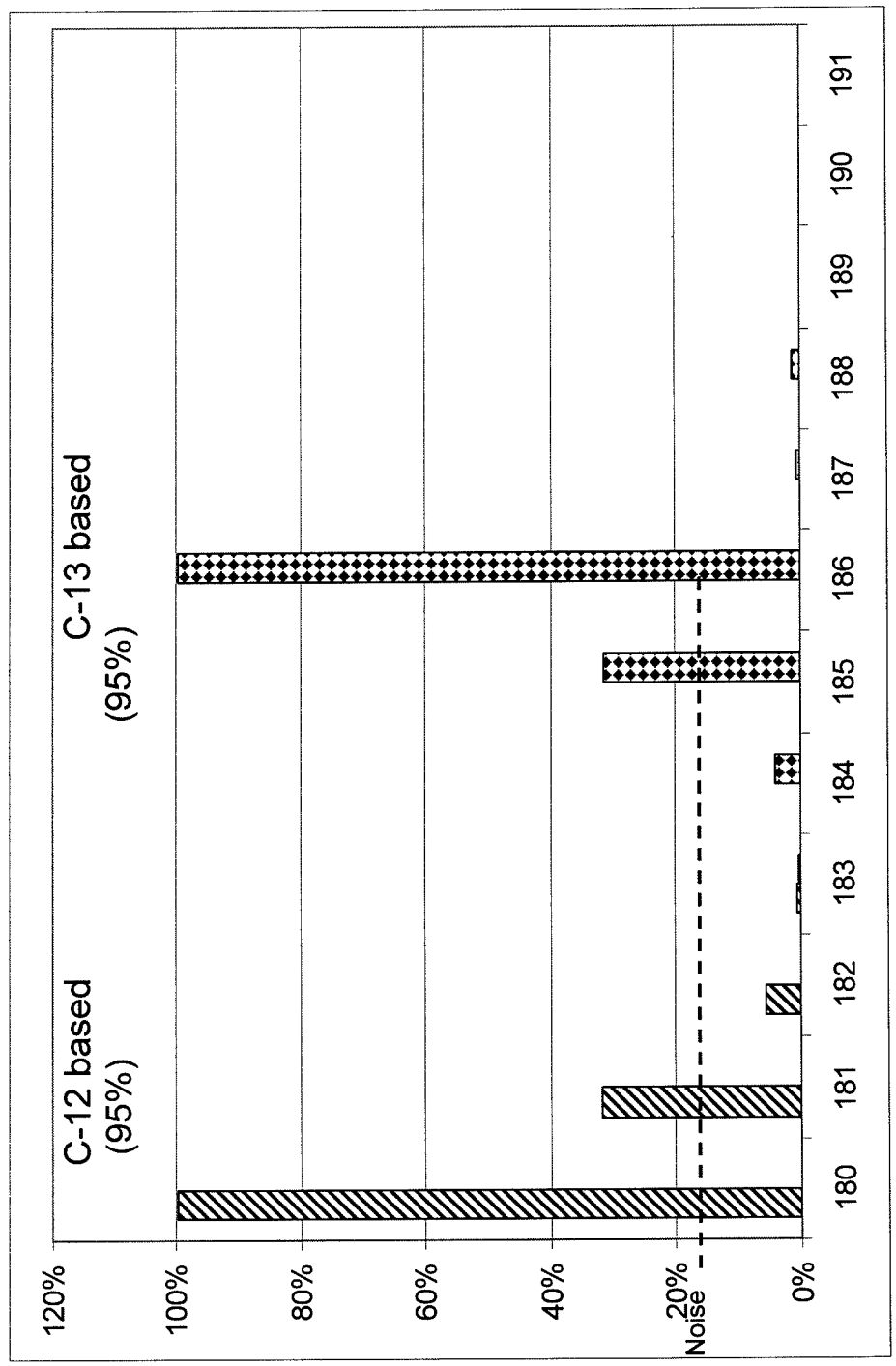
FIG. 3 illustrates a hypothetical mass spectrum for glucose showing the effects of altering the isotopic distribution on daughter ions by using non-natural abundance C-12 (95% C-12/5% C-13) on the left (diagonal lines), and altered enrichment C-13 (95% C-13 and 5% C-12) on the right (diamonds).

In the case of nearly pure isotopic starting material (see FIG. 2), the majority peak becomes even more dominant and the other peaks are even less likely to be seen. In both of the preceding cases, in a majority of the time one cannot count on seeing anything except the majority peak for each compound. Thus, in both of these cases from a composited sample, as defined above, there would be two peaks from glucose, at 180 and 181 AMU, in a mass spectrum of the sample. Based on the fact that this is a known compound and previously identified, these two could be distinguished, and if the "experimental" response caused the C-13 glucose peak to drop below detectable limits then this could be determined. However, if the compound were not glucose, but rather an unknown compound and there was only one peak it would be impossible to determine if the identified peak originated from the "control" side or the "experimental".

This invention improves upon this situation by specifically using material that is devised to assure that the minority peaks are present in sufficient quantity that they will generally be seen. In this case, the source of every compound can be identified because, relative to the majority peak, the minority peak will be larger in mass (and therefore derived from $^{12}C$ based cells), or the minority peak will have a smaller mass (and therefore be derived from the $^{13}C$ based cells). Thus, it is optimal to increase the percentage of the "impurity"; i.e., $^{12}C$ in $^{13}C$ or visa versa, in carefully controlled amounts significantly above their natural abundance (see Tables 1A and 1B, below).

TABLE 1A

| C-12 | | | | | | |
|---|---|---|---|---|---|---|
| C12 + 1% | C12 + 2% | C12 + 3% | C12 + 4% | C12 + 5% | C12 + 10% | Mol. Mass |
| 1 | 1 | 1 | 1 | 1 | 1 | 180 |
| 6.43% | 12.61% | 18.92% | 25.37% | 31.95% | 67.03% | 181 |
| 1.41% | 1.90% | 2.74% | 3.93% | 5.50% | 20.00% | 182 |
| 0.08% | 0.17% | 0.30% | 0.47% | 0.70% | 3.64% | 183 |
| 0.01% | 0.01% | 0.03% | 0.04% | 0.07% | 0.48% | 184 |
| 0.00% | 0.00% | 0.00% | 0.00% | 0.01% | 0.05% | 185 |
| 0.00% | 0.00% | 0.00% | 0.00% | 0.00% | 0.00% | 186 |
| 0.00% | 0.00% | 0.00% | 0.00% | 0.00% | 0.00% | 187 |
| 0.00% | 0.00% | 0.00% | 0.00% | 0.00% | 0.00% | 188 |
| 0.00% | 0.00% | 0.00% | 0.00% | 0.00% | 0.00% | 189 |
| 0.00% | 0.00% | 0.00% | 0.00% | 0.00% | 0.00% | 190 |
| 0.00% | 0.00% | 0.00% | 0.00% | 0.00% | 0.00% | 191 |

Table 1A shows the mass profile; i.e., the isotopic distribution, for a C-12 based compound with a molecular compound of mass 180 ($C_6H_{12}O_6$) that has been diluted with various percentages of C13. Thus, a C12-based molecule of mass 180 with 95% C-12 and 5% C-13 will have an M+1 (@ 181 AMU) that is 31.95% of the height of the parent peak at 180 AMU. It will furthermore have a M+2 that is 5.5% of the parent peak. The remaining values illustrate lesser and greater dilutions of C-12 with C-13.

TABLE 1B

| C-13 | | | | | | |
|---|---|---|---|---|---|---|
| C13 + 1% | C13 + 2% | C13 + 3% | C13 + 4% | C13 + 5% | C13 + 10% | Mol. Mass |
| 0.00% | 0.00% | 0.00% | 0.00% | 0.00% | 0.00% | 180 |
| 0.00% | 0.00% | 0.00% | 0.00% | 0.00% | 0.01% | 181 |
| 0.00% | 0.00% | 0.00% | 0.00% | 0.01% | 0.23% | 182 |
| 0.00% | 0.02% | 0.06% | 0.14% | 0.29% | 2.73% | 183 |
| 0.15% | 0.62% | 1.43% | 2.60% | 4.15% | 18.44% | 184 |
| 6.06% | 12.24% | 18.55% | 24.98% | 31.55% | 66.45% | 185 |
| 100.00% | 100.00% | 100.00% | 100.00% | 100.00% | 100.00% | 186 |
| 0.44% | 0.52% | 0.60% | 0.67% | 0.76% | 1.18% | 187 |
| 1.23% | 1.23% | 1.23% | 1.23% | 1.23% | 1.23% | 188 |
| 0.00% | 0.00% | 0.01% | 0.01% | 0.01% | 0.01% | 189 |
| 0.01% | 0.01% | 0.01% | 0.01% | 0.01% | 0.01% | 190 |
| 0.00% | 0.00% | 0.00% | 0.00% | 0.00% | 0.00% | 191 |

Conversely to Table 1A, Table 1B shows the mass profile; i.e., the isotopic distribution, for a C-13 based compound with a molecular compound of mass 186 ($C_6H_{12}O_6$) that has been diluted with various percentages of C12. Thus, a C13-based molecule of mass 186 with 95% C-13 and 5% C-12 will have an M−1 (@ 185 AMU) that is 31.55% of the height of the parent peak at 186 AMU. It will furthermore have a M−2 that is 4.15% of the parent peak. Note that this molecule will have very small M+1, etc. peaks due to isotopic contributions from other atomic species, i.e. oxygen, hydrogen, nitrogen, etc.

Thus, the compounds that are contributed to the composite from the $^{13}C$ sample can be distinguished because they have daughters that are at M−1 (trailing the parent), whereas those peaks from the $^{12}C$ samples have their daughters at M+1 (leading the parent). Using this rule one can easily distinguish the source of a peak being from a control or assayed sample.

The addition of 10% impurity ($^{13}C$ in $^{12}C$ or visa versa) results in a daughter peak that is about 66% of the size of the parent. The optimal increase over natural abundance is a function of the study in question and the average size of the molecules that the study is targeted to see, but the benefit of the augmentation of the isotopic ratios in both the $^{13}C$ and $^{12}C$ media is always a benefit.

The present method can be used to compare phenotypes of single celled or multi-celled organisms. Illustratively, the single celled organisms are obtained from a cell culture. Those cells can be plant cells such as algal cells, yeasts or fungi such as *Saccharomyces cerevisiae* and *Picia pastoris*, bacteria such as the Gram-negative facultative anaerobic organism *E. coli*, or the Gram-positive organisms *Staphylococcus aureus, Streptococcus (S). sobrinus*, and *S. mutans*. The organism can also be a multi-celled organism such as a higher plant like a tree or flowering ornamental plant, or an animal such as a nematode (*Caenorhabditis elegans*), a laboratory rat (*Rattus norvegiensus*) or primate such as a human. Thus, eukaryotes and prokaryotes are contemplated.

Where cell wall constituent phenotypes are to be compared among single celled organisms, the samples can be taken from cell lysis supernatants or pellets, for example. In this situation, the standard or control, first organism cells are grown in a first nutrient medium containing predetermined amounts of first and second stable isotopes of a first atom within a nutrient, whereas the experimental second or assayed sample organism cells are grown in a second nutrient medium substantially identical to the first nutrient medium but containing different predetermined amounts, compared to the first nutrient medium, of the first and second stable isotopes of that first atom within the nutrient.

A contemplated method can also be utilized with multi-celled organisms. In this case, higher organisms such as mammals and even humans can be studied. In this instance, the standard or control sample is synthesized based upon predetermined knowledge of the majority of constituent compounds having a molecular mass of less than about 1000 AMU that are present in a representative sample such as blood, serum, muscle or bone, sap, phloem, cambium or the like, and their amounts as is appropriate to the organism and can be obtained using usual sampling techniques. The synthetic constituent compound sample contains a predetermined $^{12}C/^{13}C$ ratio such as 5/95 in each of the constituent compounds. Where possible, the assayed organism is grown on a nutrient medium containing an inverted ratio of $^{12}O/^{13}O$ such as 95/5, or the natural abundance of about 98.9/1.1. $^{12}C/^{13}C$ even though spectral analysis can be difficult with the latter ratio.

A contemplated method relies on establishing a set of relationships within a single sample that is to be analyzed. Because of the predictable form these relationships take, the entire method can be reduced to a set of algorithms that can be coded in software. This software performs these functions in an automated manner, and produces a data set that details 1) analyte compounds found in the sample, 2) the $^{12}C/^{13}C$ ratios for those analyte compounds, 3) the relevance of the compound to the response profile, 4) non-biological artifacts, and 5) derivatives of exogenously applied compounds.

At its most fundamental the methods described impose patterns in the final data set that can be used in the interpretation of the data set to achieve a greater degree of precision, and accuracy than can be achieved by any other method. However, it is one thing to create these patterns, and another to use them.

As is well known in the art, analysis of the mass spectra is typically accomplished with the aid of so-called "peak-picker" software that is designed to identify and report mass spectral ion peaks. This software is available commercially, in open access, and from private workers. One such program is disclosed in Katajamaa et al., BMC *Bioinformatics* 2005, 6:179doi:10.1186/1471-2105-6-179, whereas another is disclosed in Rögnvaldsson et al., 2004 *J. Chrom. B*, 807(2, August 5):209-215; doi:10.1016/j.jchromb.2004.04.010. Commercial products are illustrated by those available under the name RAZOR TOOLS/6™ from Spectrum Square Associates, 755 Snyder Hill, Ithaca N.Y. 14850 USA.

The software that is required in using the patterns created must be aware of the nature of the patterns created and then seek them in the final data set. In one such application, a composite sample is provided and is subjected to a separation phase, such as a GC, HPLC or other chromatographic separation. The effluent of the separation is then analyzed by mass spectroscopy. The patterns are buried in the raw mass spectrometer data set as a series of scans with each scan representing a sequential time segment.

The algorithm used to seek the patterns can take many forms; however, in one instance
1) all of the ions seen by the mass spectrometer at a single point in time (scan, or possibly a de-convoluted peak) are gathered into a subset;

2) the analyte ions in this subset are initially sorted by their m/z values, and then are then resorted based on their height or amplitude;

3) the pattern of ions (from top to bottom) is examined to determine where the slope of the ion trace becomes approximately level. This point defines random noise, and all further ions are considered "noise". Noise ions are removed from consideration.

4) Starting from the ions with the greatest height or amplitude, the individual ions are examined (queried by the software) sequentially:
   a) For each ion (that has m/z or mass of M)
     i. Does the M+1 have the size compatible with its being based on a C-12 majority molecule; i.e., with 3% to 10% C-13 overall incorporation? In this situation, the M+1 will be between 18%, 31%, or 66% if the molecule has a mass of approximately 180 and has 3%, 5%, or 10% C-13 content, respectively. If so, the analyte ion is identified as a C-12 majority molecule and all associated ions (M+1, M+2, etc.; similarly identified) are removed from future consideration. The next highest available analyte ion is then examined.
     ii. Does the M−1 have the size compatible with its being based on a C-13 majority molecule; i.e., with 3% to 10% C-12 overall incorporation? In this situation, the M−1 will be between 18%, 31%, or 66%, respectively, if the molecule has a mass of approximately 180 and has 3%, 5%, or 10% C-13 content. If so, this analyte is identified as a C-13 majority molecule and all associated ions (M−1, M−2, etc.; similarly identified) are removed from future consideration. The next highest available ion is thereafter examined.
     iii. Does the M+2 demonstrate a pattern associated with a standard? If so, it is identified as a standard and all associated ions (M+2, etc.) are removed from future consideration. The next highest available analyte ion is thereafter examined.
     iv. If none of the above are true, the analyte ion is derived from an artifact and not experimentally significant. It is removed from further consideration.
   b) This process is repeated until all analyte ions at this time point (and not yet accounted for) are analyzed.

5) Steps 1 to 4 will be repeated for all time points.

6) The outcome of the above process identifies all analyte ions as either derived from a C-12 majority molecule, a C-13 majority molecule, a standard or removes them from consideration.
   a) All analyte ions are now grouped in time to form peaks (if this has not already been done. In other manifestations this can be done in an earlier stage.) These peak characteristics include a start time, end time, maximal time, base mass, maximal height of base ion, etc.)
   b) For all C-12 majority molecules, a matching C-13 majority molecule is sought. This matching molecule demonstrates a similar time signature; i.e., similar start time, end time, and maximal time. Values to collect include:
     i. The mass difference between the C-12 majority base mass and the C13 majority base mass represents the number of carbons in the molecule.
     ii. The ratio between the maximal height of the C-12 majority molecule and the maximal height of the C13 majority molecule.
   c) For all standards, their time is noted.

7) Alignment of all pairs can be accomplished by standard methods for calculating or normalizing retention indices (illustratively by use of the internal standards).

8) The mean and standard deviation for the ratio values for all pairs is calculated.

9) All pairs that deviate outlier ratios are identified by evaluation of their deviation from the mean. This final step of the evaluation can vary according to experimental design and analytical conditions.

There are many possible ways of rearranging the steps described here or accomplishing each of their outcome but they all will need to accomplish the majority of the above steps.

A library containing a plurality of member profiles of phenotypic isotopic ratios of different organisms is also contemplated. The individual member profiles of the library can be phenotypic ratios of strains, varieties, species or genera of organism such as bacteria, yeast, fungi, algae, higher plants or animals such as *E. coli, S. aureus, S. cerevisiae, P. pastoris, cyanobacteria*, green alga and red alga, or the like. The library members can also be of a single genus so that one can determine if an unknown organism of the genus *Escherichia* is *E. adecarboxylata, E. albertii, E. blattae, E. coli, E. fergusonii, E. hermannii*, or *E. vulneris*. It is to be understood that such libraries can be prepared for substantially any type of organism.

A contemplated library contains a plurality of member profiles of phenotypic isotopic ratios of different organisms. Each member profile is a plurality of mass spectrally-obtained ratios of first isotope to second isotope that are present in each analyzed analyte peak relative to the median isotopic ratio of a composite sample.

That composite sample is comprised of an admixture of substantially equal amounts of first and second samples. The first sample is a standard (control) sample that is comprised of average concentrations of a majority of constituent compounds having a molecular mass of less than about 1000 AMU that are present in a representative sample of a first organism. Each constituent compound is comprised of the same, first predetermined amounts of first and second stable isotopes of a first atom. The second sample is an assay (test) sample that is comprised of constituent compounds of having a molecular mass of less than about 1000 AMU that are present in a representative sample of the organism whose phenotype is assayed. Each constituent compound is comprised of the same, second predetermined amounts of first and second stable isotopes of said first atom. The first and second predetermined amounts of first and second isotopes are different from each other, and the first and second isotopes are other than H or D.

A contemplated method is general in its applicability and is illustrated by the following specific examples.

ILLUSTRATIVE EXAMPLES

Example 1

*E. coli* Assay

In this instance the experimental design is set up to compare bacterial cultures to determine whether they are the same or different strains. In this instance, because of the nature of the question to be answered, the appropriate control is a contemporaneous culture.

Actively growing cultures of two *Escherichia coli* (*E. coli* bacteria) are subjected to one or more wash/rinse cycle(s) using an isotonic but non-nutritional (IN) buffer (via centrifugation). The first culture is of a known strain, whereas the second culture is of an unknown strain. The resulting pellets of cells are re-suspended in the same IN buffer and apportioned to create two sets of 12 samples that they have an equal or approximately equal number of bacterial cells.

The IN buffer is removed from these 24 samples. Two identical media are prepared, in one (herein called "C13 medium") the sole carbon source is isotopically enriched $^{13}$C-glucose (as discussed above), and in the other (herein called "C12 medium") the sole carbon sources is isotopically enriched $^{12}$C-glucose (as discussed above).

Twelve samples of the first culture are washed three times with the C13 medium and the remaining 12 samples of the culture to be assayed are similarly washed with the C12 medium. After the final wash, the cells are dispensed into a vessel suitable for growth and in which the only medium available is either the C12 or C13 medium in which the cells were last washed.

By performing the above steps, one prepares two sets of 12 identical cultures, each of which has approximately the same number of the statistically similar cells, but half of which use C12 medium for growth (herein referred to as "C12 samples") and the remainder use C13 medium for growth (herein referred to as "C13 samples"). For purposes of this illustration, the C13 samples are deemed the control and the C12 samples are the culture to be assayed, although in practice this can be reversed. The important point is that the samples be handled so that for each C13 sample there is an equivalent C12 sample.

Both sets of samples are grown until they reach exponential growth and have undergone several cellular divisions. The cells/organisms are harvested at specified times thereafter, and the samples are matched up. The C13 (control) and the C12 (assayed) matched samples are combined during the harvest process to create a single composite sample. In this example three separate composites can be created at time 0, 1, 4, and 24 hours, respectively.

The cells of the composite samples are lysed and the lysate fractionated on a size-exclusion column or HPLC or GC to provide samples whose solute molecules (analytes) have a maximal molecular weight of less than about 1000 AMU. A detailed mass spectral analysis is performed on the composite samples.

The individual C12/C13 ratios for each analyte ion are determined as is the average (or the mean or median) value for the whole composite sample. The relative C12/C13 ratios of the analytes of each sample (of known or unknown identity) are determined. The statistical variance of the ratios sample is determined.

An analyte compound that has a C12/C13 ratio that is a significant deviation (two or more standard deviations) from the median ratio is indicative of a difference in phenotype. For example, if the average ratio for the analytes is 1 (1:1 C12/C13 ratio), but some analytes have ratios of 10 (10:1) or 0.1 (1:10) then the analytes that are outliers to the general population, e.g., those with ratios of 10 and 0.1, are those that most strongly indicate a point of biochemical alteration.

Because each genetic variant produces a distinctive pattern relative to a "standard" control, one can not only characterize the differences but also create a "library" of such differences to characterize the non-control organism. The construction of such libraries requires only that the conditions for growth be tightly controlled and be reproducible.

Example 2

Multi-Celled Organisms-*C. elegans*

The experimental design is set up to assay an animal, for illustration here the nematode, *Caenorhabditis elegans* (*C.*

*elegans*). Because of the nature of the question to be answered, the appropriate control is an aliquot of the time zero organism, which in this instance is one hour after the application of second round of fresh media.

An actively growing culture of a control *C. elegans* and its feedstock of is subjected to one or more wash/rinse cycle(s) using an isotonic but non-nutritional (IN) buffer (via centrifugation). The resulting pellet of nematodes is re-suspended in the same IN buffer. A similar procedure is used for the sample of nematodes to be assayed. Thus, 2 samples are created, each of which has an equal or approximately equal number of nematodes. The IN buffer is removed from these 2 samples.

Two identical media are prepared. In one (herein called "C12 medium"), the sole carbon source is isotopically enriched $^{12}$C-glucose (upon which the bacterial feedstock of the nematode grow), and in the other (herein called "C13 medium") the sole carbon sources is isotopically highly enriched $^{13}$C-glucose.

The assayed sample is washed three times with the C12 medium and the remaining sample is equally treated with the C13 medium. After the final wash, the nematodes are dispensed into a vessel suitable for growth and in which the only nutrient-containing medium available is either the C12 or C13 medium in which the cells were last washed.

Two identical *C. elegans* cultures, both of which have approximately the same number of organisms are thus prepared. One of the cultures uses C12 medium for growth (herein referred to as "C12 samples") and the other uses C13 medium for growth (herein referred to as "C13 samples"). (For purposes of this illustration, the C13 sample is the control culture and the C12 sample is the sample that is to be assayed. The important point is that the samples be handled so that there is an equivalent C12 sample for the C13 sample. Both samples should be permitted to grow until they reach exponential growth and have undergone at least 1 or 2 full generations. After the appropriate growth period, the C13 sample has its medium removed and replaced with fresh C13 medium. The C12 sample is similarly treated and also be given fresh medium.

After the appropriate subsequent growth period, the C13 sample has its medium removed and replaced with fresh C13 medium and the nematodes separated for age. Only the youngest stage is permitted to proceed. The C12 sample is similarly treated and also be given fresh medium.

After a one hour period has passed (T=0), the C13 culture is aliquotted to 24 equal portions and nematodes in each aliquot harvested and frozen (as the controls). Three of the C12 (assayed) cultures are similarly harvested at time (T=0) and the harvested nematodes added to their matched C13 harvested controls. Additional triplicate sets of the nematodes are harvested at T=24, T=48, T=120 hours. As these nematodes are harvested they are paired with their matched T=0 samples to create the composite samples. The composite samples are quick frozen in liquid nitrogen for storage. The frozen samples are ground, thawed and admixed with distilled water or other aqueous dispersant, and then the dispersed sample so prepared is into its components by mass, and those having a molecular weight of about 1000 AMU or less are further separated and the resulting separated analytes are assayed by mass spectroscopy as discussed above.

A detailed analysis (metabolomic, proteomic, transcriptomic, or analysis for any other carbon-based class of compounds) is performed on the composite samples. The individual C12/C13 ratios for each analyte ion are determined as is the average (or median) value for the whole composite sample. The relative C12/C13 ratios of the analytes of each sample (of known or unknown identity) are determined. The statistical variance of the ratios sample is determined. An analyte compound that has a C12/C13 ratio that is a significant deviation (two or more standard deviations) from the average ratio is indicative of a difference in phenotype between the two nematodes examined.

Example 3

Lab Rat Comparisons

Humans, along with other large organisms, represent an extreme case in that it is extremely unlikely that a C-13 based subject will ever be achieved. Therefore, it is necessary to manufacture a synthetic mixture of C-13 based compounds that approximates the required sample. This is accomplished by establishing average concentrations of a majority of constituent compounds in a representative population and creating a mixture to this specification.

Where biological diversity of the organism is high, it is useful to create the "Averaged" sample. In the case of a larger organism this can only be approximated by creating an "average" sample through a synthetic admixture of appropriate compounds at appropriate concentrations using appropriate isotopic balances.

This preparation of an averaged sample can necessitate the compositing of individual samples to form a "biologically averaged" Experimental and control sample. In this example, the experimental design is set up in order to determine the effect of physiological stress (induced by fasting for 24 hours) on an animal, for illustration here the rat, *Rattus norvegiensus*. Because of the nature of the question to be answered, the appropriate control is a composite sample of rat plasma and the experimental sample is a composite sample of rat plasma from rats that have undergone the experimental treatment, which in this example will be starvation for 24 hours. In a like manner, animals with induced infectious diseases can be compared to disease-free animals, or animals having diabetes can be compared to normal, non-diabetic animals, and the like. Due to the nature of the experiment it is expedient that the control population is the C-13 animal as the control need not be contemporaneous and can be a standard control that is available prior to the actual running of the experiment.

Because the test system consists of animals, the assay has more noise due to the greater variance inherent in the source material. The use of sample averaging partially offsets this problem as it averages the inherent biological variability, thus rendering the samples more representative of the norm. This results in a simplified experimental design, although it requires more complex prior preparation.

At the age of 6 weeks, the experimental animals are subjected to the experimental condition, for illustration here fasting for 24 hours beginning at the time that the light-cycle starts. Therefore, the experiment samples, plasma samples, are taken at the beginning of the light cycle on the following day.

All of the samples from the experimental group are similarly collected.

A composite (in this case, average) experimental sample is created by mixing equal aliquots of plasma from all experimental animals.

The control samples have been similarly collected and composited (in this case, average) from animals that have been feed a C-13 equivalent diet.

By performing steps 1 through 5 one should end up with two similar samples which contain the required information content, namely the definition of the experimental response condition and the definition of the control condition. This creates the pair of sample to be mixed to create the composite sample for analysis.

A detailed analysis (metabolomic, proteomic, transcriptomic, or analysis for any other carbon-based class of compounds) is performed on the composite sample. The individual C12/C13 ratios for each analyte ion are determined, as is the average (or median) value for the whole composite sample. The relative C12/C13 ratios of the analytes of each sample (of known or unknown identity) are determined. The statistical variance of the ratios sample is determined. An analyte compound that has a C12/C13 ratio that is a significant deviation (two or more standard deviations) from the average ratio is indicative of a difference in phenotype between the two laboratory rat populations examined.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method for assaying phenotypic similarity or dissimilarity of an assayed organism compared to that of a standard organism comprising the steps of:
   (a) providing a composite sample comprised of an admixture of substantially equal amounts of first and second samples,
   said first sample being a standard sample that is comprised of average concentrations of a majority of constituent compounds having a molecular mass of less than about 1000 AMU that are present in a representative sample of the organism species whose phenotype is to be assayed, said constituent compounds (i) being dissolved or dispersed in a first liquid medium, and (ii) each constituent compound being comprised of the same first predetermined amounts of $^{12}C$ and $^{13}C$, wherein $^{12}C$ is present at 1 to 10 percent of the total carbon present in said constituent compounds,
   said second sample being an assay sample that is comprised of constituent compounds having a molecular mass of less than about 1000 AMU that are present in a representative sample of the organism whose phenotype is to be assayed, said constituent compounds (i) being dissolved or dispersed in a second liquid medium, and (ii) each constituent compound being comprised of the same second predetermined amounts of $^{12}C$ and $^{13}C$, wherein $^{13}C$ is present at 1 to 10 percent of the total carbon present in said constituent compounds, said first and second predetermined amounts of $^{12}C$ and $^{13}C$ being different from each other whereby isotopic patterns of analyte peaks are created on mass spectral analysis indicative of the sample from which each analyte is derived;
   b) mass spectroscopically analyzing said composite sample for isotopic patterns of analyte peaks to identify a majority isotopic peak of the first sample and a majority isotopic peak of the second sample, for each analyzed analyte;
   (c) determining the ratio of the majority analyte peak from said first sample to the majority analyte peak from said second sample for each analyzed analyte, to determine an isotopic peak ratio for each analyzed analyte;
   (d) determining the composite sample median analyte peak isotopic ratio; and
   (e) determining the phenotypic similarity or dissimilarity of the assayed organism to the standard organism by comparing the isotopic peak ratio determined in step (c) for each analyzed analyte with the composite sample median analyte peak isotopic ratio, wherein an assayed organism whose analyte isotopic peak ratios significantly deviate from the composite sample median analyte peak isotopic ratio is phenotypically dissimilar from the standard organism, and an assayed organism whose analyte isotopic peak ratios do not significantly deviate from the composite sample median analyte peak isotopic ratio is phenotypically similar to the standard organism.

2. The method according to claim 1, wherein the isotopic peak ratio is determined for fewer than all analytes observed.

3. The method according to claim 1, wherein the first and second liquid media are aqueous.

4. A method for identifying phenotypic similarity or dissimilarity of an assayed organism to that of a standard organism of the same species comprising the steps of:
   (a) providing a first standard sample that is comprised of average concentrations of a majority of constituent compounds having a molecular mass of less than about 1000 AMU that are present in a representative sample of the organism species whose phenotype is to be assayed, said constituent compounds (i) being dissolved or dispersed in a first aqueous medium, wherein $^{12}C$ is present at 1 to 10 percent of the total carbon and (ii) each constituent compound being comprised of the same first predetermined amounts of $^{12}C$ and $^{13}C$, wherein $^{12}C$ is present at 1 to 10 percent of the total carbon present in said constituent compounds of said first aqueous medium,
   (b) providing a second, assay sample comprised of constituent compounds having a molecular mass of less than about 1000 AMU that are present in the organism whose phenotype is to be assayed, said constituent compounds (i) being dissolved or dispersed in a second aqueous medium and (ii) each constituent compound being comprised of the same second predetermined amounts of $^{12}C$ and $^{13}C$, wherein $^{13}C$ is present at 1 to 10 percent of the total carbon present in said constituent compounds of said second aqueous medium, said first and second amounts of $^{12}C$ and $^{13}C$ isotopes being different from each other, and being in inverted ratios of each other, whereby isotopic patterns of analyte peaks are created on mass spectral analysis indicative of the sample from which each analyte is derived;
   (c) admixing substantially equal amounts of the first and second samples to form a composite sample;
   (d) mass spectroscopically analyzing said composite sample for isotopic patterns of analyte peaks to identify a majority isotopic peak of the first sample and a majority isotopic peak of the second sample, for each analyzed analyte;
   (e) determining the ratio of the majority analyte peak from said first sample to the majority analyte peak from said second sample for each analyzed analyte, to determine an isotopic peak ratio for each analyzed analyte;
   (f) determining the composite sample median isotopic analyte peak ratio; and
   (g) determining the phenotypic similarity or dissimilarity of the assayed organism to the standard organism by comparing the ratio determined in step (e) for each analyzed analyte with the composite sample median analyte peak isotopic ratio, wherein an assayed organism whose analyte isotopic peak ratios significantly deviate from the composite sample median analyte peak isotopic ratio is phenotypically dissimilar from the standard organism, and an assayed organism whose analyte isotopic peak ratios do not significantly deviate from the composite sample median analyte peak isotopic ratio is phenotypically similar to the standard organism.

5. The method according to claim 4, wherein said assay sample is obtained from a cell culture.

6. The method according to claim 5, wherein said cell culture is comprised of plant cells.

7. The method according to claim 6, wherein said plant cells are algal cells.

8. The method according to claim 6, wherein said plant cells are higher plant cells.

9. The method according to claim 5, wherein said cell culture is comprised of bacterial cells.

10. The method according to claim 5, wherein said cell culture is comprised of animal cells.

11. The method according to claim 4, wherein said assay sample is obtained from a plant.

12. The method according to claim 4, wherein said assay sample is obtained from an animal.

13. The method according to claim 4, wherein $^{12}C$ constitutes 90 to 98.9% of that element in one sample.

14. The method according to claim 4, wherein said first standard sample is a synthetic sample that is prepared based upon predetermined knowledge of the majority of constituent compounds having a molecular mass of less than about 1000 AMU that are present in a representative sample of the first organism and the amounts of those constituents.

15. The method according to claim 5, wherein said cell culture is comprised of yeast cells.

16. The method according to claim 4, wherein $^{13}C$ is present at 5 percent of the total carbon present in said constituent compounds of said second aqueous medium.

* * * * *